United States Patent [19]

Ponsford

[11] 4,179,562
[45] Dec. 18, 1979

[54] 2,4-DIAMINO-5-ALKYLOXY-PYRIMIDINES

[75] Inventor: Roger J. Ponsford, Horsham, England

[73] Assignee: Beecham Group Limited, England

[21] Appl. No.: 815,565

[22] Filed: Jul. 14, 1977

[30] Foreign Application Priority Data

Jul. 29, 1976 [GB] United Kingdom ............... 31582/76

[51] Int. Cl.² .......................................... C07D 239/48
[52] U.S. Cl. ..................................... 544/298; 424/251
[58] Field of Search ................. 260/256.4 N; 544/325, 544/298

[56] References Cited

U.S. PATENT DOCUMENTS

| 3,105,074 | 9/1963 | Mamalis ............................... 544/206 |
| 3,723,429 | 3/1973 | Mamalis et al. ....................... 424/249 |

OTHER PUBLICATIONS

Falco et al., J. Amer. Chem. Soc. 73 (1951), pp. 3753–3758.

Burger, *Medicinal Chemistry*, 3rd Ed., (1970) pub. by Wiley-Interscience, pp. 479–502.

*Primary Examiner*—Paul M. Coughlan, Jr.
*Attorney, Agent, or Firm*—Jacobs & Jacobs

[57] ABSTRACT

Compounds of the formula

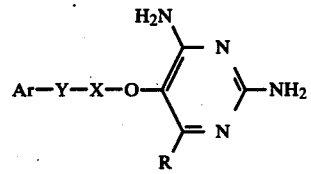

and pharmaceutically acceptable salts thereof and antimalarial and antibacterial compositions containing an effective amount of active agent and a pharmaceutically acceptable carrier particularly in oral dosage form wherein R is hydrogen, methyl or ethyl; X is alkylene of 1–10 carbon atoms; Y is oxygen, sulphur or a bond, and Ar is an optionally substituted aryl moiety; are useful for their antimalarial and antibacterial activity.

26 Claims, No Drawings

2,4-DIAMINO-5-ALKYLOXY-PYRIMIDINES

The present invention relates to pyrimidine derivatives, their preparation and compositions containing them.

U.S. Pat. No. 3,723,429 discloses inter alia that compounds of the formula (I):

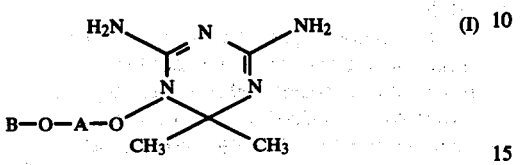

wherein A is a divalent aliphatic group and B is an optionally substituted hydrocarbon group hve antimicrobial activity. Such compounds are not particularly well distributed in the body after oral administration to mammals and so it would be of advantage if a class of compounds of similar activity could be found that were better distributed but not more toxic after oral administration. Such a group of compounds has now been discovered.

Accordingly the present invention provides the compounds of the formula (II):

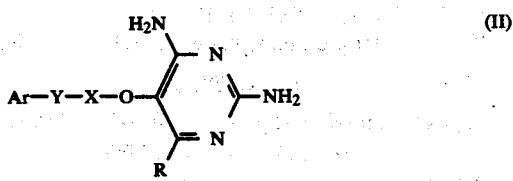

and pharmaceutically acceptable salts thereof wherein R is a hydrogen atom or a methyl or ethyl group; X is an alkylene group of 1 to 10 carbon atoms; Y is O, S or a bond; and Ar is an aryl group.

The alkylene group X may be straight or branched chain but is most suitably straight chained. Particularly suitable groups X include those of the formula—$(CH_2)_n$—where n is an integer of from 1 to 6.

Most suitably Y is an oxygen atom.

Suitable groups Ar include phenyl, naphthyl, anthranyl, phenanthryl and phenyl substituted by from 1 to 5 groups selected from fluorine, chlorine, bromine, lower alkoxyl, lower acyloxyl, lower alkyl, lower alkenyl, $C_{5-6}$ cycloalkyl, $C_{5-6}$ cycloalkenyl or lower alkylthio.

When used herein the term 'lower' means that the group contains 1-6 carbon atoms.

Particularly suitable compounds of the formula (II) include those of the formula (III):

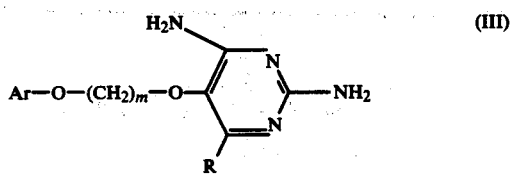

and pharmaceutically acceptable salts thereof wherein R and Ar are as defined in relation to formula (II) and m is 1, 2, 3 or 4.

Favoured values for the group Ar include the phenyl and naphthyl groups and phenyl substituted by one two or three groups selected from chlorine, bromine, lower alkoxyl, lower alkyl, lower alkenyl, $C_{5-6}$ cyclolkyl and $C_{5-6}$ cycloalkenyl.

One particularly suitable sub-group of compounds of the formulae (II) and (III) is that wherein R is a hydrogen atom.

Another particularly suitable sub-group of compounds of the formulae (II) and (III) is that wherein R is a methyl group.

Certain favoured compounds of the formulae (II) and (III) include those wherein Ar is a phenyl, mono-, di- or tri- substituted phenyl especially phenyl substituted by cyclohexyl or cyclopentyl and optionally substituted by a further 1 or 2 groups.

Particularly favoured compounds of the formulae (II) and (III) include those wherein Ar is a group of the sub-formula (a):

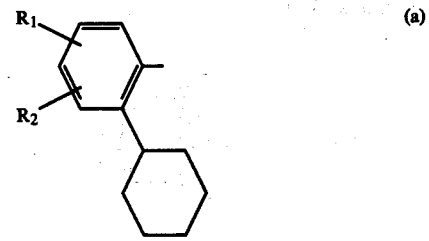

wherein $R_1$ is a hydrogen, fluorine, chlorine or bromine atom or a methyl or methoxyl group and $R_2$ is a hydrogen, fluorine, chlorine or bromine atom or a methyl or methoxyl group.

Most suitably $R_1$ is a hydrogen, chlorine or bromine atom.

Most suitably $R_2$ is a hydrogen chlorine or bromine atom.

Certain preferred moieties of the sub-formula (a) are those of the sub-formula (b):

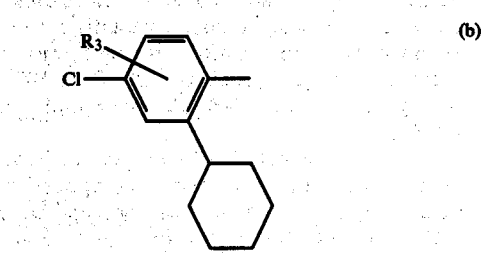

wherein $R_3$ is a hydrogen, fluorine, chlorine or bromine atom or a methyl or methoxyl group.

More suitably $R_3$ is a hydrogen, chlorine or bromine atom.

Preferably $R_3$ is a hydrogen atom.

The acid addition salts of the compounds of the formula (II) may be any formed with a pharmaceutically acceptable inorganic or organic acid such as hydrochloric, orthophosphoric, acetic, succinic, lactic, citric, fumaric, tartaric or the like acid.

In a further aspect the present invention provides a process for the preparation of the compounds of the formula (II) and their salts which process comprises the reaction of a compound of the formula (IV):

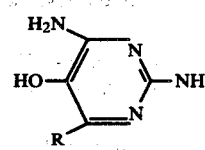

or a basic salt thereof wherein R is a hydrogen atom or a methyl or ethyl group; and a compound of the formula (V):

wherein Ar, Y and X are as defined in relation to formula (II) and Z is a group readily displaceable by a nucleophile.

An alternative process of this invention for the preparation of those compounds of the formula (II) wherein Y is O comprises the reaction of a compound of the formula (VI):

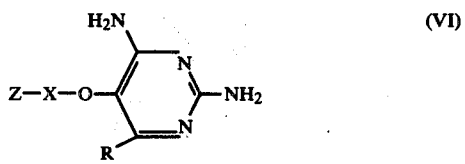

wherein R and X are as defined in relation to formula (II) and Z is as defined in relation to formula (V) with a compound of the formula (VII):

or a basic salt thereof wherein Ar is as defined in relation to formula (II).

Suitable groups Z include Cl, Br, I, $OSO_2CH_3$, $OSO_2C_6H_4CH_3$ and the like.

Suitable basic salts of the compounds of the formulae (IV) or (VII) include alkali metal salts such as the sodium salt and other similar salts.

The preceding reactions are normally carried out in relatively polar organic solvents such as dimethylformamide, dimethylsulphoxide, acetonitrile and the like. Normally the condensations are performed at a non-extreme temperature such as $-20°$ C. to $180°$ C., more usually from $10°$ C. to $100°$ C., for example from $25°$ C. to $60°$ C.

The present invention also provides a pharmaceutical composition which comprises a compound of the formula (II) and a pharmaceutically acceptable carrier.

Most suitably the composition will be adapted for oral or injectable administration. Preferred compositions will be adapted for oral administration.

The compositions may be formulated by conventional methods, for example as described in U.S. Pat. No. 3,723,429.

Particularly suitable compositions of this invention include tablets, capsules and other unit dosage forms which contain from 5 mg to 500 mg of active compound. Such compositions may be administered once or more times a day in order to provide a daily dose of 20–1000 mg and more usually 50–500 mg for a 70 kg adult.

The compositions of this invention may be used to treat malaria and/or bacterial infections. The compositions are of especial usefulness as they are able to effectively treat malarial infections which are resistant to many conventional anti-malarial agents. The good oral absorption properties of the compositions of this invention are an additional advantage that allows for their easy use.

The compositions of this invention may also be used to treat bacterial infection as they possess antibacterial activity, for example against gram positive bacteria such as *Staphylococcus aureus* and against gram negative bacteria such as *Escherichia coli* and *Proteus mirabilis*.

If desired the compositions of this invention may also contain an antibacterially active sulphonamide such as sulphamethoxazole.

The hydroxy compounds of the formula (IV) may be prepared by the method of R. Hull, Journal of the Chemical Society, 1965, 2033.

The following Examples illustrate the invention:

EXAMPLE 1

2,4-Diamino-6-methyl-5-(4-chloro-2-cyclohexyl-phenoxypropyloxy)pyrimidine 2,4-Diamino-6-methyl-5-hydroxypyrimidine dihydrochloride (2.13 g) was added to a solution prepared from sodium (0.8 g) and ethanol (30 ml) and stirred at room temperature for one hour. 4-Chloro-2-cyclohexylphenoxypropyl bromide (3.32 g) was added portionwise and the reaction mixture was stirred overnight. The reaction was heated at $50°$ C. for 24 hours, cooled, filtered and the filtrate evaporated. The residue was triturated with acetone and filtered. The crude product was dissolved in ethanol and a few drops of concentrated HCl added whereupon the product crystallised as a white solid. The product was recrystallised from methanol/ethanol (1.65 g; 40%), m.p. 246–7° C. Analysis indicated that the product was a monohydrochloride, possibly a monohydrate.

EXAMPLE 2

Using the method of Example 1, the compounds of the formula:

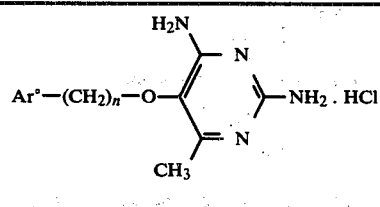

were prepared:

| Ar° | n | Crystallisation Solvent | M.P. °C. |
|---|---|---|---|
| 3,4-dichlorophenyl | 1 | aq. acetone | 240 |
| 1-naphthyl | 1 | ethanol | 252–3(½ H₂O) |
| 1-phenanthryl | 1 | methanol | 259–60 (MeOH) |

-continued

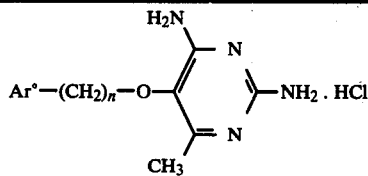

were prepared:

| Ar° | n | Crystallisation Solvent | M.P. °C. |
|---|---|---|---|
| pentachlorophenoxy | 3 | DMF/MeOH/H₂O | 279 |
| 2,3,4,6-tetrachlorophenoxy | 3 | aq. methanol | 305–7 |
| 2,4,6-trichlorophenoxy | 3 | aq. methanol | 270–1 |
| 2,4-dichlorophenoxy | 3 | aq. ethanol | 234–5 |
| 2,3-dichlorophenoxy | 3 | aq. ethanol | 280–1 |
| 2-(prop-2-enyl)-4-bromophenoxy | 3 | methanol/ethanol | 230–1 |
| 2-bromophenoxy | 3 | methanol/ethanol | 259–61 |
| 2-(prop-2-enyl)-4-methoxyphenoxy | 3 | ethanol | 232 |
| 3,4,5-trimethoxyphenoxy | 3 | ethanol | 255–6 (½ H₂O) |
| 3,4,5-trimethoxyphenoxy | 4 | methanol/ethanol | 231–2 |
| 2,6-dimethoxyphenoxy | 3 | MeOH/EtOH/H₂O | 248–50 (¼ H₂O) |
| 2,6-dimethoxyphenoxy | 2 | ethanol | 240–2 |
| 2,3-dimethoxyphenoxy | 3 | aq. ethanol | 233–5 |
| 3,4,5-trimethoxyphenyl | 3 | aq. ethanol | 245–6 |
| 3,4,5-trimethoxyphenyl | 2 | aq. ethanol | 250–1 |
| 3,4-dimethoxyphenyl | 2 | water | 227–8 |
| 3,4,5-trimethoxyphenyl | 1 | ethanol | 236–7 |
| 2-methoxyphenyl | 1 | aq. ethanol | 233 |
| 2-thioethylphenyl | 1 | aq. ethanol | 233–40 |
| phenoxy | 4 | ethanol | 245–6 (H₂O) |
| phenoxy | 6 | ethanol | 240 (½ H₂O) |
| 2,4,6-trichlorophenoxy | 4 | ethanol | 269–71 |
| 2,4,5-trichlorophenoxy | 6 | ethanol | 231–2 (½ H₂O) |
| phenoxy | 8 | acetone | 234–5 |
| 4-methoxyphenoxy | 8 | ethanol | 255–6 |
| phenoxy | 10 | ethanol | 262 |
| 2-chlorophenoxy | 10 | methanol/ethanol | 239–40 (H₂O) |
| 2,6-dimethoxyphenoxy | 10 | ethanol | 229–30 (¼ H₂O) |

EXAMPLE 3

Using the method of Example 1, the compounds of the formula:

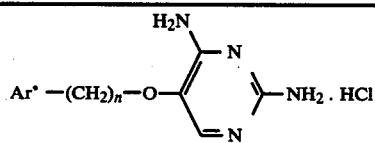

were prepared:

| Ar° | n | Crystallisation Solvent | M.P. °C. |
|---|---|---|---|
| 1-naphthyl | 1 | ethanol | 189 (1½ H₂O) |
| 1-phenanthryl | 1 | aq. ethanol | 253–4 (2HCl) |
| pentachlorophenoxy | 3 | aq. methanol | 253–4 |
| 3,4,5-trimethoxyphenyl | 1 | aq. ethanol | 245 |
| 3,4,5-trimethoxyphenyl | 2 | aq. ethanol | 242 (H₂O) |
| phenoxy | 10 | ethanol | 174–5 (1½ H₂O) |
| 3,4-dimethoxyphenyl | 2 | ethanol | 238–9 |

EXAMPLE 4

PHARMACOLOGY

The compound of Example 1 was administered to a group of mice at a dose of 160 mg/kg. No deaths occured indicating that the compound was less acutely toxic than pyrimethamine. After oral administration to mice in a standard antimalarial test (Rane Test) the compound of Example 1 was found to be half as active as pyrimethamine.

What I claim is:

1. A compound of the formula (II):

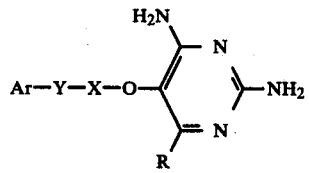

or a pharmaceutically acceptable salt thereof wherein R is hydrogen, methyl or ethyl; X is alkylene of 1 to 10 carbon atoms; Y is O or S; and Ar is phenyl, naphthyl, anthranyl, phenanthryl or phenyl substituted by from 1 to 5 substituents selected from the group consisting of fluorine, chlorine, bromine, lower alkoxyl, lower acyloxyl, lower lkyl, lower alkenyl, cycloalkyl of 5 or 6 carbon atoms, cycloalkenyl of 5 or 6 carbon atoms and lower alkylthio.

2. A compound according to claim 1 wherein X is straight chained alkylene when X contains more than one carbon atom.

3. A compound according to claim 1 wherein X is —(CH₂)ₙ— wherein n is an integer from 1 to 6.

4. A compound according to claim 1 wherein Y is oxygen.

5. A compound according to claim 1 of the formula (III):

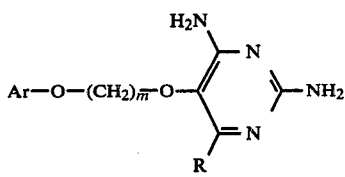

(III)

or a pharmaceutically acceptable salt thereof wherein R is hydrogen, methyl or ethyl; Ar is phenyl, naphthyl, anthranyl, phenanthryl or phenyl substituted from 1 to 5 substituents selected from the group consisting of fluorine, chlorine, bromine, lower alkoxyl, lower acyloxyl, lowr alkyl, lower alkenyl, cycloalkyl of 5 or 6 carbon atoms, cycloalkenyl of 5 or 6 carbon atoms and lower alkylthio: and m is 1, 2 3 or 4.

6. A compound according to claim 5 wherein m is 2 or 3.

7. A compound according to claim 5 wherein Ar is phenyl, naphthyl or phenyl substituted by one, two or three substituents selected from the group consisting of chlorine, bromine, lower alkoxyl, lower alkyl, lower alkenyl, cycloalkyl of 5 or 6 carbon atoms and cycloalkenyl of 5 or 6 carbon atoms.

8. A compound according to claim 1 wherein R is hydrogen.

9. A compound according to claim 1 wherein R is methyl.

10. A compound according to claim 1 wherein Ar is phenyl, mono-substituted phenyl, di-substituted phenyl or tri-substituted phenyl.

11. A compound according to claim 10 wherein Ar is phenyl substituted by cyclohexyl or di- or tri-substituted phenyl wherein one substituent is cyclohexyl.

12. A compound according to claim 1 wherein Ar is a group of the sub-formula (a):

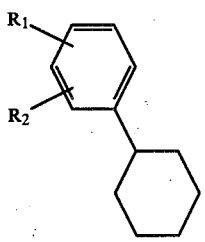

wherein $R_1$ is hydrogen, fluorine, chlorine, bromine, methyl or methoxyl and $R_2$ is hydrogen, fluorine, chlorine, bromine, methyl or methoxyl.

13. A compound according to claim 12 wherein $R_1$ is hydrogen, chlorine or bromine.

14. A compound according to claim 12 wherein $R_2$ is hydrogen, chlorine or bromine.

15. A compound according to claim 12 wherein Ar is a group of the sub-formula (b):

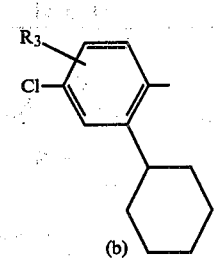

wherein $R_3$ is hydrogen, fluorine, chlorine, bromine, methyl or methoxyl.

16. A compound according to claim 15 wherein $R_3$ is hydrogen, chlorine or bromine.

17. A compound according to claim 16 wherein $R_3$ is hydrogen.

18. The compound according to claim 1 which is 2,4-diamino-6-methyl-5-(4-chloro-2-cyclohexylphenoxypropyloxy) pyrimidine or a pharmaceutically acceptable acid addition salt thereof.

19. The compound according to claim 1 which is the monohydrochloride salt of 2,4-diamino-6-methyl-5-(4-chloro-2-cyclohexylphenoxypropyloxy) pyrimidine.

20. A compound according to claim 10 wherein Ar is phenyl substituted by cyclohexyl or cyclopentyl or di- or tri-substituted phenyl wherein one substituent is cyclohexyl or cyclopentyl.

21. A compound according to claim 1 in the form of a pharmaceutically acceptable salt selected from the group consisting of the hydrochloride, orthophosphate, acetate, succinate, lactate, citrate, fumarate or tartrate.

22. A compound according to claim 5 in the form of a pharmaceutically acceptable salt selected from the group consisting of the hydrochloride, orthophosphate, acetate, succinate, lactate, citrate, fumarate or tartrate.

23. A compound of the formula:

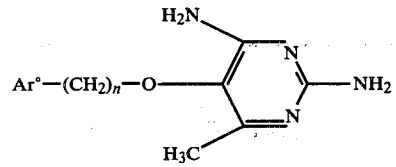

or a pharmaceutically acceptable acid addition salt thereof wherein $Ar^o$ and n have the following values:

| $Ar^o$ | n |
| --- | --- |
| pentachlorophenoxy | 3 |
| 2,3,4,6-tetrachlorophenoxy | 3 |
| 2,4,6-trichlorophenoxy | 3 |
| 2,4-dichlorophenoxy | 3 |
| 2,3-dichlorophenoxy | 3 |
| 2-(prop-2-enyl)-4-bromophenoxy | 3 |
| 2-bromophenoxy | 3 |
| 2-(prop-2-enyl)-4-methoxyphenoxy | 3 |
| 3,4,5-trimethoxyphenoxy | 3 |
| 3,4,5-trimethoxyphenoxy | 4 |
| 2,6-dimethoxyphenoxy | 3 |
| 2,6-dimethoxyphenoxy | 2 |
| 2,3-dimethoxyphenoxy | 3 |
| phenoxy | 4 |
| phenoxy | 6 |
| 2,4,6-trichlorophenoxy | 4 |
| 2,4,5-trichlorophenoxy | 6 |
| phenoxy | 8 |
| 4-methoxyphenoxy | 8 |
| phenoxy | 10 |
| 2-chlorophenoxy | 10 |
| 2,6-dimethoxyphenoxy | 10 |

24. A compound of the formula:
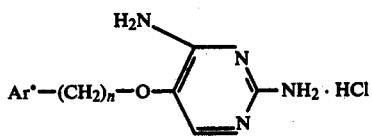
wherein Ar° and n have the following values:
| Ar° | n |
|---|---|
| pentachlorophenoxy | 3 |
| phenoxy | 10 |
25. 2,4-Diamino-6-methyl-5-(4-chloro-2-cyclohexyl-phenoxypropyloxy) pyrimidine or a pharmaceutically acceptable acid addition salt thereof.
26. The compound of claim 25 wherein the acid addition salt is a hydrochloride salt.
* * * * *